United States Patent
Viebach et al.

[11] Patent Number: 6,077,219
[45] Date of Patent: Jun. 20, 2000

[54] ROLL-BACK TUBE SYSTEM

[75] Inventors: Thomas Viebach, Pischertshofen; Gerhard Weiglhofer, Schwabhausen/Weil; Robert Pauker, Kissing; Gerhard Buchmann, Berg; Fritz Pauker, Wiffertshausen/Friedberg, all of Germany

[73] Assignee: STM Medizintechnik Starnberg GmbH, Schwabhausen/Weil, Germany

[21] Appl. No.: 09/065,653

[22] Filed: Apr. 23, 1998

[30] Foreign Application Priority Data

Apr. 23, 1997 [DE] Germany ............... 197 17 108

[51] Int. Cl.⁷ .................................................. A61B 1/01

[52] U.S. Cl. ................................. 600/114; 604/271

[58] Field of Search ......................... 600/101, 102, 600/104, 114, 115, 116, 153, 156; 604/95, 96, 172, 271

[56] References Cited

U.S. PATENT DOCUMENTS

| 5,045,070 | 9/1991 | Grodecki et al. | 604/271 |
| 5,236,423 | 8/1993 | Mix et al. | 600/115 |
| 5,259,364 | 11/1993 | Bob et al. | 600/115 |
| 5,586,968 | 12/1996 | Grundl et al. | 600/114 |

*Primary Examiner*—John P. Leubecker
*Attorney, Agent, or Firm*—Graybeal Jackson Haley LLP

[57] ABSTRACT

A roll-back tube system, preferably for an endoscope, for moving an inner shaft which is guided in a roll-back tube of the type that is rolled back at both ends. The tube is driven via a number of friction wheels, suction cups or tracks which act on an inner tube section in order to drive the system in a continuous movement. In order to seal off the gap between the shaft and the inner tube section, front and rear turn-back areas in each case form a bead which bears sealingly on the shaft. The admission of lubricant into the gap between shaft and inner tube section takes place via an essentially radial shaft bore in the area of the roll-back tube, which shaft bore is either connected to an external admission line via the shaft cavity or an inner line, or else via a rear clamping piece by means of a lubricant injection shoe adapted to the shaft surface.

27 Claims, 7 Drawing Sheets

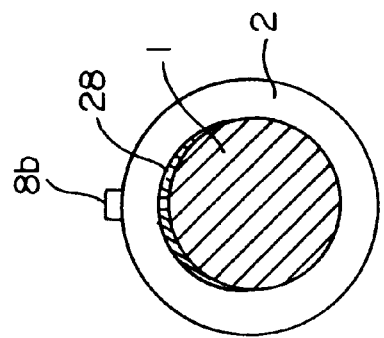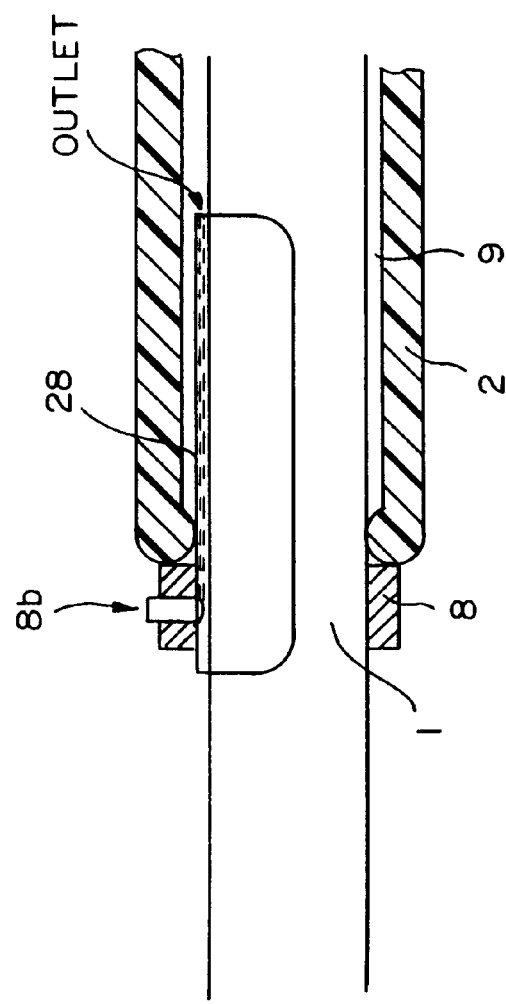

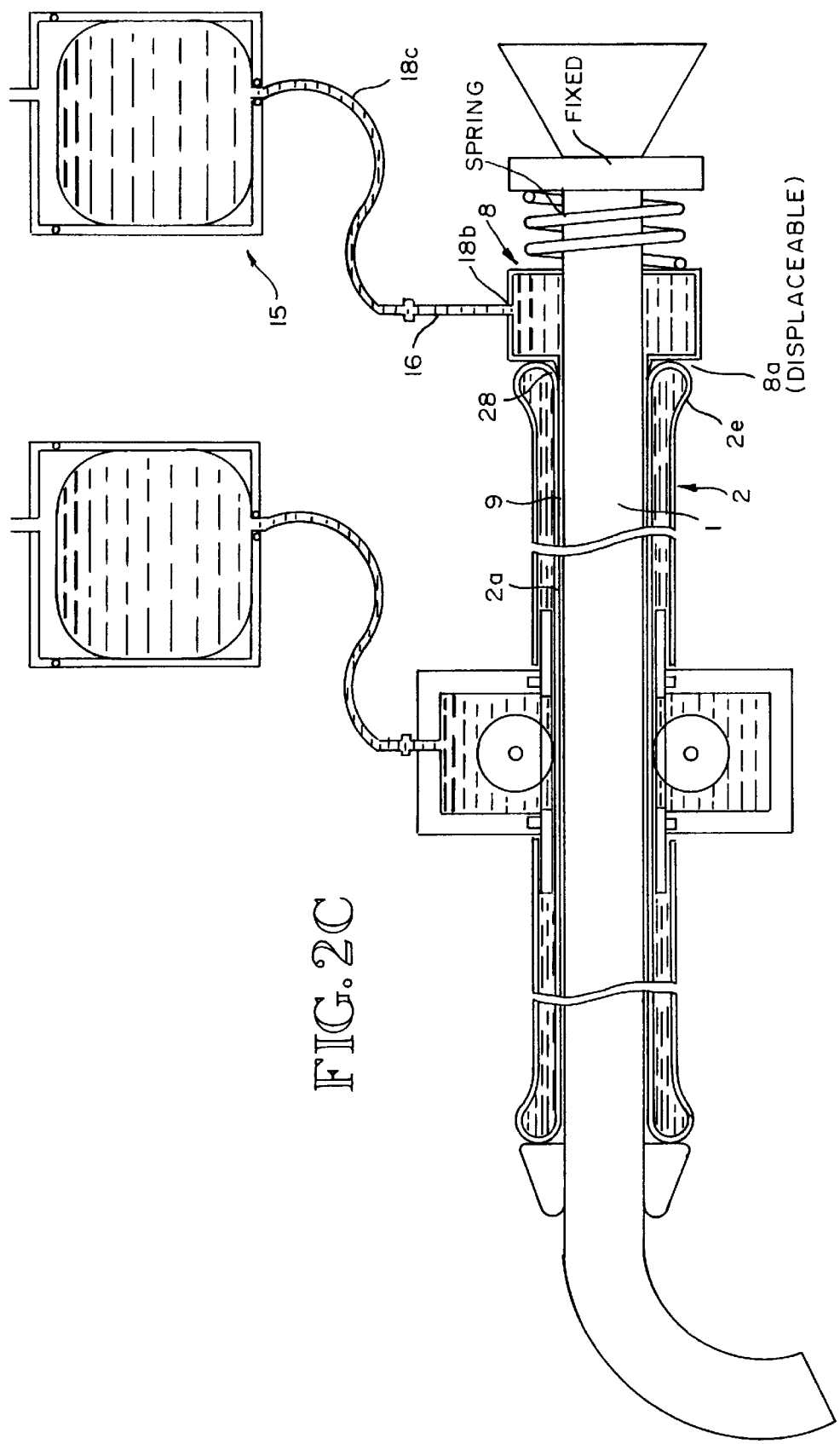

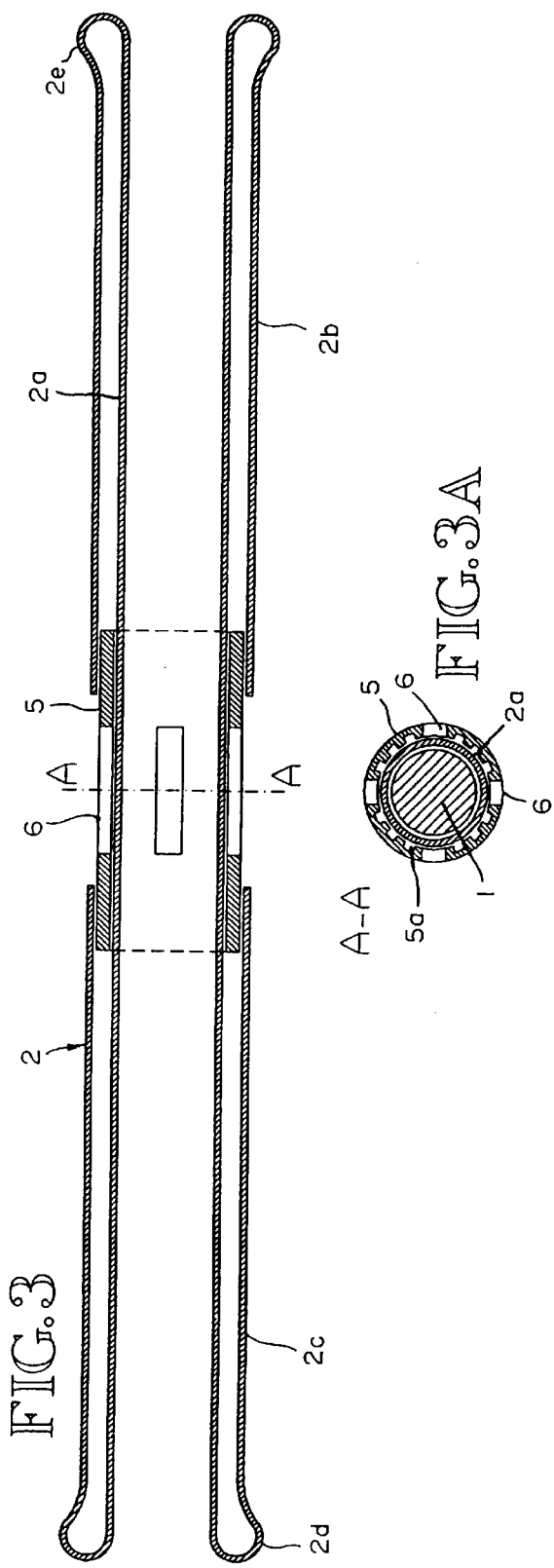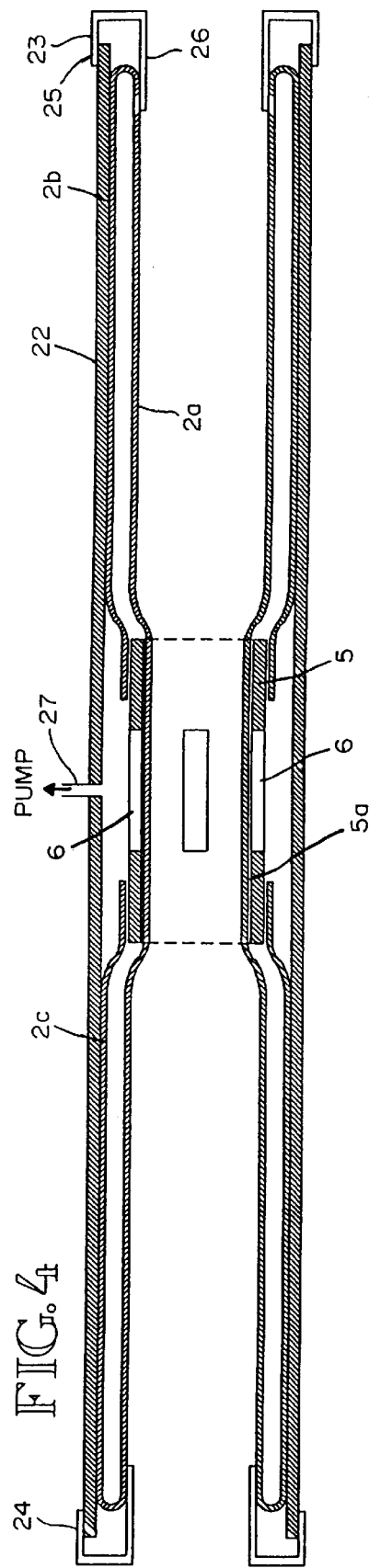

ROLL-BACK TUBE SYSTEM

FIELD OF THE INVENTION

The invention relates to the construction of a roll-back tube system, preferably for an endoscopy apparatus for examining channel-shaped cavities, for example in the human body.

BACKGROUND OF THE INVENTION

Endoscopes are mainly used for visually examining the esophagus, the stomach, the intestine (from the stomach or from the anus), the urethra and the bladder. For this purpose, the endoscope is equipped at its distal end with a lighting device and with an optic, preferably a camera chip, which is connected via leads inside an endoscope shaft to a camera control means at the end of the endoscope shaft. The camera control means is in turn connected via a video processor to an external monitor on which the operating physician can identify the areas to be examined. The distal end of the shaft to be introduced into the cavity is here designed so that it can be bent in any direction, and it can be angled, much like a finger, manually by means of a handle, preferably via two control wheels with brake at the rear end section of the endoscope. In addition, the endoscope shaft generally has at least two channels passing through it, and opening out at the frontmost point of the distal end. When so required, these channels can be used for passing though cleaning fluid, for example, in order to clean an area which is to be examined, or $CO_2$ (air) for opening out the cavity, or else various working instruments can be pushed through a working channel, for example forceps or scissors for removing tissue specimens, biopsy needles, heatable cutting wires, coagulation electrodes, which can likewise be manually operated at the rear end of the endoscope shaft via operating wires or Bowden cables inside the inner channel. When removing a tissue specimen, after the distal end has reached the location in question, forceps for example are introduced into the channel from the direction of the rear section of the endoscope shaft and are advanced to the distal end. After the specimen has been removed, the forceps are drawn back again and removed from the channel so that further examination can be continued.

The endoscope generally has an elongate tubular shape, with a diameter of about 9 to 15 mm, and consists of a flexible material so as to be able to follow the curvatures of the cavity which is to be examined, for example intestinal loops.

An endoscope of this generic type is presently known from the prior art, for example in accordance with DE 4,242,291 A1.

This endoscope essentially consists of an endoscope head or distal end, which is adjoined by an endoscope shaft consisting of a flexible bendable tubular body, and an operating mechanism at the rear end of the endoscope shaft. The operating mechanism has a number of operating wheels which are mounted rotatably on the endoscope shaft and which are operatively connected to the distal end via operating wires or Bowden cables which are run through the inside of the endoscope shaft. Moreover, in a rear end section of the endoscope there is provided a first drive or advance mechanism which exerts a driving force on the endoscope shaft via drive wheels.

Arranged around the endoscope shaft, at least in its front section, there is a roll-back tube which is driven by a second drive or advance mechanism. The roll-back tube here consists of an inner tube section which bears slidably on the jacket surface of the endoscope shaft and is turned back in the area of the distal end of the endoscope to form a front outer tube section. The front outer tube section is also guided back as far as the second drive mechanism and fixed to the housing thereof. In the rear area of the endoscope, the inner tube section is turned back to form a rear outer tube section, which is likewise guided to the second drive mechanism and fixed to the housing thereof, on the axial end side directed away from the front outer tube section.

The second drive mechanism here acts on the inner roll-back tube section in order to move the latter in the axial direction of the endoscope shaft. For this purpose, the second drive mechanism has a type of cuff or collar which can be contracted in the radial direction and thus pressed with friction onto the inner tube section and can also be moved in the axial direction of the endoscope in the manner of a piston. The radially acting pressing force of the cuff is in this case chosen to be so great that at least some of the applied pressing force is transmitted, by a material deformation of the inner tube section, to the jacket surface of the endoscope shaft, so that the endoscope shaft is driven together with the inner roll-back tube.

Since, with this type of drive alone, effected by the second drive mechanism, the speed of advance (and travel) of the roll-back tube at its front roll-back area would, because of its roll-back movement, be only half as great as that of the endoscope shaft, i.e. the endoscope shaft would, with increasing depth of penetration, emerge telescopically from the roll-back tube, the first drive mechanism, mentioned in the introduction, exerts a braking force on the endoscope shaft, which braking force counteracts the advancing force of the second drive mechanism.

The second drive mechanism is in this case synchronized with the first drive mechanism in such a way that, in the interaction of the two drive mechanisms, the speed of movement of the inner tube section in an axial direction is twice as great as the speed of movement of the endoscope shaft, this sliding relative to the inner endoscope shaft (i.e. the distal end of the endoscope shaft moves at the same speed as the turn-back area of the roll-back tube).

In order to facilitate the relative sliding movement between the endoscope shaft and the roll-back tube, the prior art according to DE 4,242,291 A1 further provides a lubricating device by means of which a lubricant can be forced in between the inner tube section and the endoscope shaft and also between the inner and outer tube sections. For this purpose, the lubricating device has a cone-shaped sleeve which is slipped over the endoscope shaft and interacts sealingly with the rear roll-back area of the roll-back tube, which rides up onto the cone-shaped sleeve. The lubricant, which is forced by means of a pump into the gap between the cone-shaped sleeve and the endoscope shaft, spreads out between the inner tube section and the endoscope shaft along the entire length, and excess amounts of lubricant in the front turn-back area of the roll-back tube emerge into the cavity which is to be examined.

It has now been shown that the endoscope according to DE 4,242,291 A1 has, particularly in respect of the driving of the roll-back tube and the endoscope shaft, and also in respect of the relatively high losses of lubricant through leakage in the front turn-back area of the roll-back tube, certain faults which make the use of the endoscope difficult.

Thus, in particular, the above-described second drive mechanism proves to be disadvantageous, since the pressing force which is transmitted over a large surface area from the cuff to the endoscope shaft, via the elastically deformed roll-back tube, leads to a considerable impairment of the relative slidability of the endoscope shaft inside the roll-back tube, despite the admission of lubricant. To this extent, an increased braking force has to be applied to the endoscope shaft by the first drive mechanism in order to maintain the speed ratio between roll-back tube and endoscope shaft of 2:1. Moreover, the first advance mechanism can be synchronized only with some difficulty, and thus cost, with the piston-like advance movement of the second advance mechanism. It is thus evident that the first drive mechanism not only has to be dimensioned to give high output, and accordingly also be of large design, but also that a greater control outlay is entailed. Moreover, the piston movement the little suited to positioning the distal end exactly at a location which is to be examined.

It is known from a further prior art, in particular according to DE 3,925,484 A1, to design the distal end of the endoscope shaft with a mushroom-shaped head piece having a concave sealing surface which is directed toward the roll-back area of the roll-back tube and which, as the roll-back tube is being driven, is in sealing engagement with its roll-back area. However, this design necessitates a widening of the endoscope shaft, in particular of the distal end, and thus once again to impaired handling of the endoscope.

SUMMARY OF THE INVENTION

It is therefore the object of the present invention to develop a roll-back tube system which, (inter alia), is suitable for an endoscope of the generic type, in such a way that its functionality and handling are improved.

The roll-back tube system of the invention has a shaft which is slidably guided in a tube rolled back at both ends and which in turn can be moved by means of a drive mechanism which acts on the inner tube section of the roll-back tube. According to the invention, the drive mechanism has at least one continuously driving advancing means which can be pressed radially onto the inner tube section in order to move this essentially continuously in the axial direction of the shaft. This has the great advantage that the continuous advance of the roll-back tube system can be exactly controlled and thus, for example, the distal end of an endoscope can be guided exactly to the target location.

A feature of the invention provides that the pressing force of the advancing means on the inner tube section is chosen such that the shaft is in direct frictional contact with the inner tube section, at least in the area of the advancing means.

A preferred embodiment provides that the pressing force of the advancing means on the inner roll-back tube section deforms the latter to such an extent that the shaft forms an abutment for the advancing means.

It is intended that the advancing means are one or more friction wheels which can be prestressed against the inner tube section with a predetermined or adjustable pressing force. By this means it is ensured that the endoscope shaft is advanced into the cavity within a patient in a movement which is on the one hand continuous and on the other hand as slip-free as possible. Alternatively, the friction wheels can be replaced, for example, by a suction cup drive or by a crawler mechanism.

In addition to the forgoing features, the drive mechanism may include a device for synchronizing the shaft movement with the movement of the roll-back tube. In a preferred embodiment, this is a rear and front end-piece or clamping piece which is fixed axially on the shaft, and on which the rear or front roll-back area of the roll-back tube bears firmly and slidingly, depending on the direction of advance, so that the roll-back tube, via the rear or front end-piece, applies a braking force to the shaft counter to the already existing advancing force. Alternatively to this, the synchronizing device can be a roller or spindle drive which acts on the rear end section of the shaft and is synchronized with the roll-back tube drive in such a way that the speed of advance of the shaft amounts to half the speed of advance of the inner tube section.

The invention solves the initially set object also by means of a roll-back tube system herein which the roll-back tube has a tube-guiding part or sleeve made of a rigid material, which sleeve is drawn over the inner tube section to form an annular gap, and at the two axial end sections of which the free ends of outer tube sections are fixed, which sections are formed by turning back the inner tube section and bringing it back at two axially spaced roll-back areas. This sleeve now provides a receiving or fastening possibility for a drive mechanism directly on the inner tube section, so that the outer dimension of the whole roll-back tube system remains compact and, thus, handling is improved.

The invention may also provide that the sleeve has in its central section a number of openings or longitudinal slots which are preferably arranged at the same angular distance from each other. The roll-back tube thus forms, by way of the inner tube section, the outer tube sections and the sleeve, a cavity which is sealed off from the environment and can only be accessed via the openings in the sleeve. In this way, the sleeve is structurally prepared for the application of a drive mechanism whose advancing means can be brought into contact with the inner tube section through the longitudinal slots. In addition, the sleeve is provided with grooves which extend essentially in the axial direction and open out at the end faces of the sleeve. While the system is in operation, these grooves facilitate the obligatory movement of the lubricant, located in said cavity, through the sleeve.

Another embodiment of the invention provides for achieving the set object, that the drive mechanism of the roll-back tube system according to the invention has a two-part, fold-up housing which can be placed like a cuff around the sleeve of the roll-back tube and, in the folded-up state, forms, together with the sleeve, a cavity which is sealed off tight from the outside and in which friction wheels are accommodated, which wheels, mounted on the housing, can be pressed against the inner tube section through the openings in the sleeve when the housing is folded up. In this way, a compact, inherently closed (integrated and not additive) construction of the system is achieved, as a result of which the handling and functionality of the cooperating parts are enhanced.

The previously described wheels may be spring-mounted on the housing in order to apply to the inner tube section a pressing force which is predetermined according to the spring force or else can be adjusted. The friction wheels can additionally be provided or designed with an anti-slip lining on their running surfaces.

It has here proven particularly advantageous if the housing of the drive mechanism is designed with an attachment for the admission of a lubricant, which can be forced via the openings of the sleeve into the cavity of the roll-back tube. In this way, it is possible on the one hand for the drive mechanism itself and, on the other hand, for the relative sliding movement of the inner and outer tube sections to be lubricated and, consequently, for the friction to be reduced.

In a further aspect of the invention, it is intended to design the roll-back tube system with a lubricating device for forcing lubricant into an annular gap between the shaft and the inner roll-back tube section, in which case at least one essentially radially extending bore or perforation is provided in the wall of the shaft and opens into the annular gap and is connected to a lubricant-delivery device. In this way it is possible, with little structural outlay, for lubricant to be delivered directly into the annular gap.

The lubricating device described may comprise a rear clamping piece which is fixed on the shaft and has at least one lubricant injection shoe. This shoe protrudes into the annular gap and thus permits injection of lubricant via a cannula formed in the shoe.

In a preferred embodiment, a lubricating system for admission of lubricant into the roll-back tube system consists, (inter alia), of one or two pressure vessels for in each case accommodating a lubricant bag or lubricant bellows, which, according to the invention, is designed as a disposable article and which can be brought into fluid communication, in each case via a coupling, with admission lines of the shaft and of the drive mechanism.

Finally, the subject matter of the invention also concerns a device and a method for preparing the roll-back tube system according to the invention, the device essentially comprising a vacuum pipe, and the method comprising the following:

inserting the roll-back tube into two half shells in which a vacuum can be established, or alternatively slipping the vacuum pipe, open at both ends, over the roll-back tube and sealing the gap between the vacuum pipe and the outer tube section by applying sealing rings or caps to the end faces of the vacuum pipe or by pressing the roll-back tube onto the vacuum pipe by means of an expansion device, establishing a vacuum in the gap between the vacuum pipe and the outer tube section and in the cavity between the outer and inner tube section via the longitudinal slots in the sleeve until the inner tube section is drawn onto the outer tube section, with widening of the internal diameter of the roll-back tube, pushing the endoscope shaft into the roll-back tube, and equalizing the pressure and removing the vacuum pipe.

BRIEF DESCRIPTION OF THE DRAWING

The invention is discussed in greater detail hereinafter on the basis of preferred illustrative embodiments and with reference to the attached drawings, in which:

FIG. 1a shows an enlargement of the connection point between an outlet tube of a pressure vessel for lubricant and an admission tube of the endoscope, FIG. 2a shows a longitudinal cutaway of the rear shaft section in an enlargement in order to illustrate the admission of lubricant, FIG. 2b shows a cross section through the rear shaft section in FIG. 2a, FIG. 2c shows a variant of the illustrative embodiment according to FIG. 2, in accordance with which the rear clamping piece has a slide part which is pressed against the roll-back tube by means of a spring, which is in turn supported on a fixed part of the clamping piece, FIG. 3 shows a roll-back tube construction, as is used in the endoscope according to the first and second illustrative embodiment, FIG. 3a shows a cross section view of a drive and guide sleeve along the section line A—A in FIG. 3, FIG. 4 shows a device for assembling the roll-back tube and the endoscope shaft by means of a vacuum pipe according to the invention or two half shells.

DETAILED DESCRIPTION OF THE PREFERRED EMBODIMENT

Figure 1:
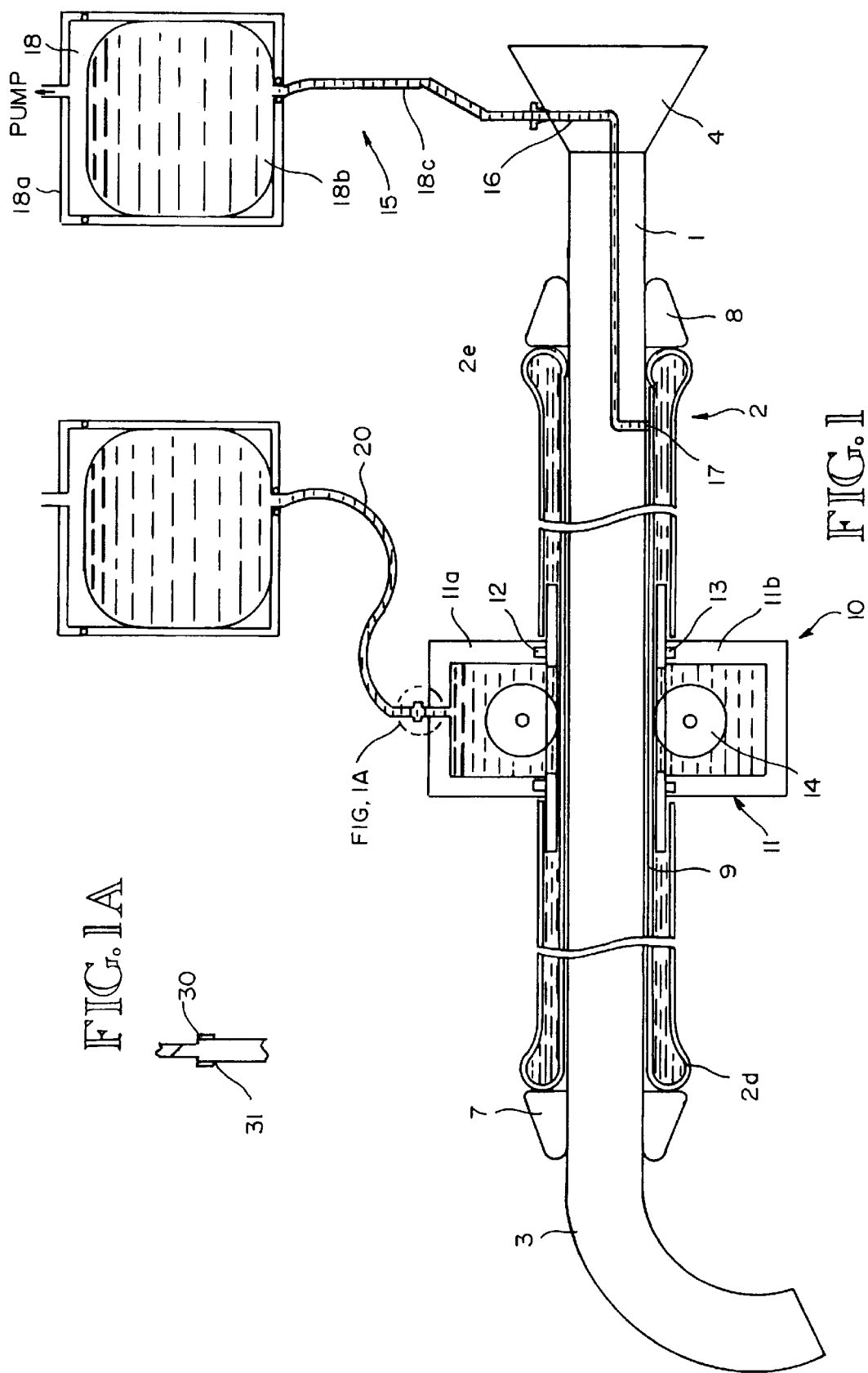
FIG. 1 shows an endoscope with integrated shaft lubrication and friction wheel drive according to a first illustrative embodiment of the invention.

The diagrammatic side elevation of an endoscope according to a first illustrative embodiment of the invention is represented in FIG. 1.

Accordingly, the endoscope according to the invention consists of an endoscope shaft 1 which is enclosed, over a length of 1 to 2 m (in general about 1600 mm), with a roll-back tube 2 of the type that is rolled back at both ends. The distal end 3 of the endoscope shaft 1 consists of an end-piece which can be angled or bent in all directions and at the tip of which a lighting device and a camera chip are arranged (neither of these shown), which is connected via electrical leads, running through the inside of the endoscope shaft 1, to a camera control means at the rear end section of the endoscope. The camera is in turn connected via a video processor to a monitor.

Alternatively to this, an optic can of course also be provided on the tip of the bendable end-piece 3 which is connected to the camera control means via light guides, for example glass-fiber bundles, within the endoscope shaft 1.

Also extending through the endoscope shaft 1 are at least two channels or tubes which open out at the frontmost point of the bendable end-piece 3 and which, at the rear end section of the endoscope, have an insertion attachment or manually controllable valves. One of these channels is used for admission of air or gas and as an admission channel for cleaning fluid for washing out areas of the cavity that are to be examined, while the other is used as a working channel for the introduction of medical instruments which can be advanced as far as the distal end in order, for example, to remove tissue specimens or to perform surgical interventions.

In order to maneuver the end-piece 3, the latter is operatively connected to a manual operating device 4 via Bowden cables (not shown) running through the inside of the endoscope shaft 1, which operating device 4 is accommodated inside a housing at an end section of the endoscope shaft 1.

As can be seen in particular from FIGS. 1 and 3, the roll-back tube 2 according to the invention consists of an inner tube section 2a, which is slideably guided through a drive and guide sleeve or tube-guiding part 5 and is turned back in its front area (turn-back area) to form a front outer tube section 2b. The front outer tube section 2b is in this case brought back to the drive and guide sleeve (tube-guiding part) 5, which is made of a rigid material, preferably a synthetic material, and is fastened at an axial end on the drive sleeve 5 in such a way that the latter comes to lie between the inner 2a and outer tube section 2b.

In a rear area (turn-back area), the inner tube section 2a is turned back to form a rear outer tube section 2c which is brought back to the drive sleeve 5 and is fixed on an axial end of the drive sleeve 5. The drive sleeve 5 is used, on the one hand, as a guiding element for the inner tube section 2a, in order to prevent warps and the formation of folds and creases, and, on the other hand, as a connection piece for the front outer 2b and rear outer tube section 2c, in which case a central area of the drive sleeve 5 remains exposed, i.e. not covered by the roll-back tube 2. In this central section the drive sleeve 5 has at least one opening, preferably a longitudinal slot 6 of predetermined width extending in the axial direction. In the present case, four longitudinal slots 6 are provided, arranged at a uniform angular distance from each other, as is shown in particular in FIG. 3a. In addition, the drive sleeve 5 according to FIG. 3a has, on its inner side, a number of continuous longitudinal grooves 5a which open out at the end faces of the drive sleeve 5. These longitudinal grooves 5a can be run either axially parallel or in a helical shape.

As can be seen in particular from FIG. 1, the material, i.e. the type of material and strength of material, of the roll-back tube 2 is chosen in such a way that a bead-shaped widening forms in each case at the front and rear roll-back areas 2d, 2e as a result of an accumulation of material at the turn-back, which bead-shaped widening leads in the inner area to a predetermined narrowing of the internal diameter of the roll-back tube 2.

According to FIG. 1, the roll-back tube 2, at its front roll-back area 2d, bears slideably on a conical front clamping piece 7 which sits securely, at least in the axial direction, on the endoscope shaft 1 and tapers conically in the direction of insertion of the endoscope. The rear roll-back area 2e of the roll-back tube 2 likewise bears slideably on a rear clamping piece 8 which, in this particular illustrative embodiment, sits securely on the endoscope shaft 1, exactly like the front clamping piece 7, and also has a corresponding shape. The rear clamping piece 8, however, tapers conically in the direction counter to the direction of insertion of the endoscope. It should be noted at this point, however, that at least the rear clamping piece 8 can have any desired external shape since it is not introduced into the cavity that is to be examined.

It can also be clearly seen from FIG. 1 that a narrow annular gap 9 is formed between the inner tube section 2a of the roll-back tube 2 and the endoscope shaft 1, which annular gap 9 is delimited axially by the two beads in the turn-back areas 2d, 2e of the roll-back tube 2, which bear sealingly on the outer jacket surface of the endoscope shaft 1.

A drive or advance mechanism 10 is arranged around the driving sleeve 5 in the central area thereof. This advance mechanism 10 consists in the present case of a housing 11, preferably made of a plastic or of a nonrusting metal alloy, in which the drive mechanism, described hereinafter, for the roll-back tube 2 according to the first, second and third illustrative embodiments of the invention is accommodated. The housing 11 itself consists of two shell-shaped housing halves 11a, 11b which, at one free edge section along the driving sleeve 5, are articulated on each other by means of a joint or hinge (not shown) and, at the opposite free edge section, can be locked by means of a locking mechanism (likewise not shown). As an alternative to this, the housing halves 11a, 11b can of course also be completely separate and can be connected by means of two locking mechanisms. On the side walls of the housing 11 running transversely with respect to the drive sleeve 5, there are, on each housing half 11a, 11b, recesses which are adapted to the outer cross sectional shape of the drive sleeve 5 and which, when the housing 11 is in the folded up and locked state, each form an inherently closed recess or opening profile corresponding to the outer contour of the drive sleeve 5 and sealingly enclose the latter from the outside. The recesses and the free edges of the housing halves 11a, 11b are provided at their respective edge surfaces with grooves 12 (not shown in further detail) into which sealing strips 13 are clamped or bonded, which, when the housing halves 11a, 11b are folded up, bear sealingly on the jacket surface of the drive sleeve 5, in order thereby to sealingly close off a housing interior.

In the present case, the drive and tube-guiding sleeve 5 has, in cross section, a circular outer contour corresponding to the circular cross section of the roll-back tube 2, in order to ensure as tight and as stress-free as possible a connection with the roll-back tube. However, it can also have a lenticular or other cross sectional shape depending on the construction of the drive mechanism.

According to the first preferred illustrative embodiment of the invention, this drive mechanism comprises a drive motor (not shown in further detail) which acts via a gear train (likewise not shown) on a number of friction wheels 14. These friction wheels 14 are each mounted on the two housing halves 11a, 11b in such a way that, in the folded-up or closed state of the housing 11, they each penetrate into a longitudinal slot 6 of the drive sleeve 5 and bear frictionally, with a predetermined pressing force, preferably adjustable via springs, on the inner tube section 2a of the roll-back tube 2. The running surface of each drive wheel 14 is preferably covered with a contact adhesion lining (coating of ceramic particles or metal granules of predetermined particle size) in order to increase the coefficient of friction between the roll-back tube 2 and the drive wheel 14. Alternatively, the friction wheels 14 can of course also be made entirely of an appropriate material, for example grind ceramic. The pressing force is moreover chosen as a function of the material and of the wall thickness of the roll-back tube 2, such that a regular and essentially slip-free advance movement of the roll-back tube 2 over the friction wheels 14 is ensured.

The endoscope according to the first preferred illustrative embodiment of the invention is moreover equipped with a lubricating system for lubricating the relative sliding movement between the endoscope shaft 1 and the inner tube section 2a, and also between the inner and outer tube sections 2a, 2b, 2c, which lubricating system is described hereinafter.

This lubricating system comprises a first lubricant delivery and admission device 15 with a compressed air pump (not shown) or a compressed air attachment which is connected to a pressure vessel 18 in order to provide this with compressed air. This pressure vessel 18 has a fold-up or removable lid 18a, by means of which a loading or unloading opening can be closed. Inside the pressure vessel 18 there is a removable or exchangeable plastic or rubber bag 18b or alternatively a lubricant bellows which is filled with the lubricant that is to be used. This bag or bellows 18b has an outlet tube 18c which is guided through a bore in the pressure vessel 18, preferably lying opposite the attachment point of the pump. The bore bears sealingly on the outlet tube 18c, for which reason, in this illustrative embodiment, a sealing strip is arranged on the bore. In addition, or as an alternative, to this seal, the bag 18 bears sealingly on the wall of the pressure vessel, so that the outlet bore is separated, by the bag 18b, in an essentially airtight manner from the attachment point of the pump, which is preferably located in the lid 18a.

Provided at the free end of the outlet tube 18c there is a coupling piece 30 which can be connected to a corresponding mating coupling piece 31 of an admission tube 16 of the endoscope, which protrudes laterally from the rear end section of the endoscope shaft 1, in particular from the housing of the operating mechanism 4. The admission tube or channel 16 is in this case, as is shown by way of indication in FIG. 1, run onwards through the inside of the endoscope shaft 1 as far as an outlet bore 17 formed in the endoscope shaft 1 in the area of the roll-back area 2.

The two coupling pieces of the outlet tube 18c and admission tube 16 are represented diagrammatically in FIG. 1a.

Accordingly, the one coupling piece 30 has a coupling flange with a union nut or a bayonet closure, the mouth of the outlet tube 18c being closed by a membrane. The other coupling piece 31 has a mating element corresponding to the union nut or the bayonet closure, as well as a cannula which is designed in a needle shape or with a cutting edge and forms the outermost end of the admission tube 16. When the two coupling pieces 30, 31 are plugged together, the cannula penetrates the membrane and thus establishes a fluid communication between the outlet tube 18c and the admission tube 16.

It should be pointed out that the arrangement of the coupling 30, 31 does not by any means need to be on the endoscope. The one coupling piece 30 can, for example, also be integrated in the bore of the pressure vessel 18, in which case the mating piece 31 can be placed directly on the bag 18b, so that when the bag 18b is fitted, a connection to the endoscope is automatically produced. The first embodiment variant is, however, to be preferred, since in this way, when the two tubes 18c and 16 are plugged together, the outlet tube 18c is already filled with lubricant along its entire length and, consequently, an additional removal of air from the lubricating system is no longer necessary.

As is also shown in FIG. 1, the admission tube 16 penetrates the outlet bore 17, in such a way that no lubricant can leak out into the inside of the endoscope shaft 1, and thus opens out into the annular gap 9 between the inner roll-back tube section 2a and the endoscope shaft 1, which is axially delimited in a fluid-tight manner by the front and rear roll-back areas 2d, 2e.

As an alternative to the above-described design of the lubricating system, it is of course also possible for the admission tube 16 or the outlet tube 18c to be connected directly to an attachment on the endoscope shaft 1, so that the delivered lubricant can spread inside the whole endoscope shaft 1. I.e., the endoscope shaft 1 in this case itself serves as part of the admission channel 16, and the lubricant is delivered to the outlet bore 17 via the admission tube 16 and the endoscope shaft 1. In this case all the "innards" of the endoscope shaft 1 then have to be covered with a special coating or insulation or have to be guided in channels in order to prevent contamination and thus associated damage caused by the relatively aggressive lubricant. Instead of the at least one outlet bore 17, it is of course also possible to provide perforation of the endoscope shaft 1 at the appropriate location, in which case a dedicated lubricant line 16 with a plurality of outlets to the shaft surface can be run through the endoscope shaft 1.

The delivery pressure of the first lubricant delivery device 15 is chosen such that the dynamic pressure arising inside the annular gap 9 between the endoscope shaft 1 and the inner tube section 2a is smaller than the bearing pressure of the bead-shaped turn-back areas 2d, 2e of the roll-back tube 2 on the endoscope shaft 1. In this case the turn-back areas 2d, 2e cooperate with the shaft 1 directly as seals, which prevent leakage of lubricant. This additionally has the advantage that this type of seal does not for the time being have to slide along the endoscope shaft 1 or with corresponding bearing pressure on the front end-piece 7, but, in accordance with the system, rolls along the endoscope shaft 1, as a result of which there is no increase in the necessary advancing force on the inner tube section 2a for overcoming frictional forces. This in turn leads to a reduction in the necessary pressing force of the friction wheels 14 on the inner tube section 2a. In this way it is also ensured that the endoscope shaft 1 remains rotatable inside the roll-back tube 2, so that it is still possible to advance through the intestine in the presence of abnormal intestinal loops.

In addition, the lubricating system comprises a second lubricant delivery and admission device 19 which is connected to the housing 11 of the drive mechanism 10 via an admission tube or channel 20. The structural design of the second lubricant delivery and admission device 19 corresponds in principle to that of the first lubricant delivery and admission device 15, and the described alternatives thereto, so that at this point reference may be made to the corresponding passages in the text.

However, as has already been indicated, the second lubricant delivery and admission device 19 is connected to the drive housing 11 in order to force the delivered lubricant into the tightly closed interior of the drive housing 11, in which case the coupling is arranged directly on the housing 11. This lubricant morover has access, via the openings or longitudinal slots 6 in the drive sleeve 5, into the cavity between the inner and outer tube sections 2a, 2b, 2c of the roll-back tube 2, in order thereby to lubricate the relative sliding movement between the inner and outer tube sections 2a, 2b, 2c. In addition to this, the lubricant of course also provides lubrication of the drive mechanism, i.e. the mounting of the friction wheels 14 themselves, inside the drive housing 11.

The endoscope according to the first preferred illustrative embodiment of the invention is prepared for operation in the manner described in detail hereinafter with reference to FIG. 4:

At the start of the procedure a vacuum pipe 22, open at both ends, is drawn over the prefabricated roll-back tube 2, its internal diameter being slightly greater than the external diameter of the outer tube section 2b, 2c. Two sealing cuffs 23, 24 are then placed over the end edges of the vacuum pipe 22. The outer part 25 of each sealing cuff 23, 24 thus lies sealingly on the jacket surface of the vacuum pipe 22, while an inner part 26 of the cuffs 23, 24 acts against the inner tube section 2a and forces this outward in a radial direction, i.e. in the direction of the outer tube section 2b, 2c. In this way a space, closed off tight from the outside, is created between the vacuum pipe 22, the sealing cuffs 23, 24 at the ends, and the outer tube section 2b, 2c of the roll-back tube 2, which is further connected, via the longitudinal slots 6 and the grooves 5a in the drive sleeve 5, to the cavity between the outer and inner tube section 2a, 2b, 2c.

As an alternative to this design, the vacuum pipe 22 can also be divided lengthwise into two half shells which are either articulated on each other along one lengthwise edge, so that they can be folded up, or are completely separate. In this way, the insertion of the roll-back tube 2 is made easier. In addition, the sealing cuffs 23, 24 can be replaced by an active expansion device (not depicted) which is not shown in detail, by means of which the roll-back areas 2e and 2d of the roll-back tube 2 can be pressed against the vacuum pipe 22. This expansion device has, similar to a filling forceps, a number (three) of expansion elements which are inserted into the tube opening at the front and rear roll-back areas 2d, 2e. In a subsequent working stage, these stoppers are moved essentially radially outward, as a result of which the tube 2 is pressed sealingly against the inner wall of the pipe. The sealing action of this expansion device can be further increased by the vacuum pipe having at both ends, an appropriate, for example cloverleaf-shaped, inner contour which ensures that the tube not only bear at the locations at which the expansion elements engage, but also between these locations on the inner wall of the pipe.

Finally, the vacuum pipe 22 can also be shaped in such a way that it has, in the area of the drive sleeve 5, a cavity corresponding to the housing 11 of the drive mechanism, so that the entire roll-back tube system consisting of roll-back tube, drive sleeve and drive mechanism can be inserted in a preassembled state into the vacuum pipe.

According to FIG. 4, the vacuum pipe 22 moreover has a line attachment 27, preferably in the area of the drive sleeve 5, which line attachment 27 is connected to a vacuum pump (not shown) via a line. When the vacuum pump is in operation, air is sucked from the cavity between the vacuum pipe 22 and the outer tube section 2b, 2c and between the outer and inner tube section 2a, 2b, 2c via the opening 6 and the longitudinal grooves 5a of the drive sleeve 5, in which case the inner tube section 2a bears against the outer tube section 2b, 2c and thereby increases the internal diameter of the roll-back tube 2 also in the area of the front and rear turn-backs 2d, 2e. The endoscope shaft 1 can now be inserted easily into the thus expanded roll-back tube 2, and this insertion procedure can be additionally facilitated by coating the shaft 1 with a lubricant.

Once the endoscope shaft 1 has been correctly positioned inside the roll-back tube 2, the vacuum pump is switched off to again equalize the pressure in the abovementioned cavities, and the inner tube section 2a again contracts to its original internal diameter and the beads at the ends in the turn-back areas 2d, 2e bear sealingly against the endoscope shaft 1. The assembling of the endoscope shaft 1 and the roll-back tube 2 is completed by removing the sealing cuffs 23, 24 and withdrawing the vacuum pipe 22.

As regards the function and operation of the endoscope according to the first illustrative embodiment of the invention, the following is stated:

To insert the endoscope, or the endoscope shaft 1, into the patient's intestine via the anus, the drive mechanism, i.e. the drive housing 11, is fitted on a base which is vertically adjustable and can be swiveled in all directions relative to a plate on which the patient is at least partially lying, so that the distal end 3 of the endoscope shaft 1 can be adapted to the individual anatomy of the patient. The distal end 3 of the endoscope shaft 1 is then inserted, i.e. a short distance into the anus, until the roll-back tube 2 has passed the sphincter muscle. CO2 gas is then fed via the endoscope shaft 1, or a channel guided therein, into the intestine in order to widen the latter out, after which the drive mechanism 10 is activated in order to drive the friction wheels 14 at a predeterminable speed of rotation or at one that can be changed during operation. Corresponding to this speed of rotation, the inner tube section 2a is advanced slowly in the direction of insertion of the endoscope, in which case it turns back at the front turn-back area 2d continuously to form the front outer tube section 2b and can thus laterally line the wall of the intestine. At the same time, the driving force of the friction wheels 14 is also transmitted to the endoscope shaft 1, since, by means of the bearing force of the friction wheels 14 on the relatively soft inner roll-back tube section 2a, the latter is pressed onto the endoscope shaft 1 and entrains the latter by frictional forces, despite the lubricant spreading between them. I.e., by means of the advance of the inner tube section 2a, the endoscope shaft 1 is entrained by frictional forces between the roll-back tube 2 and the shaft 1, and if appropriate also slightly by pressure forces in the direction of advance between the front turn-back area 2d and the front clamping piece 7 of the endoscope shaft 1, and is thus inserted into the intestine.

In order to ensure that the speed of advance of the endoscope shaft 1 does not exceed the speed of insertion of the roll-back tube 2, as has already been mentioned in detail in the introductory part of the description, a retention or braking of the endoscope shaft 2 relative to the inner tube section 2a is necessary. This takes place, in the present case, via the rear clamping piece 8, on which the rear turn-back area 2e of the roll-back tube 2 bears, which moves necessarily at the same speed as the front turn-back area 2d and which thus synchronizes the speed of advance of the endoscope shaft 1 relative to the speed of insertion of the roll-back tube 2 (i.e. the rear clamping piece 8, which sits firmly on the endoscope shaft 1, holds the latter back and in so doing leads the force of reaction into the rear roll-back tube section 2c). The speed of insertion of the roll-back tube 2 is accordingly the same as that of the endoscope shaft 1.

At this point it should be noted that during the procedure of synchronizing the advance movements of the roll-back tube 2 and of the endoscope shaft 1, the latter slides at the front and rear beads, and also in the area of the drive sleeve 5, on the inner roll-back tube section 2a, in which case, however, the speed of sliding of the endoscope shaft 1 in relation to the front and rear beads, i.e. at the turn-back areas 2d and 2e, or in relation to the inner tube section 2a, corresponds only to the relative speed of both component, which is only half as great as the absolute speed of the inner roll-back tube section 2a.

In order to ensure, in this context, that the braking forces on the rear turn-back area 2e are not allowed to become too great, and thus, if desired, in order to prevent compaction of the roll-back tube 2 in the rear outer tube section 2c as a result of the braking forces to be applied, it is necessary to keep the frictional forces between the endoscope shaft 1 and the inner tube section 2a as low as possible.

As has already been described above, an almost continuous film of lubricant builds up in the annular gap 9 between the shaft 1 and the inner tube section 2a, also in the area of the drive mechanism 10, which film does not just permit an advance of the endoscope shaft 1 essentially by the friction wheels 14, but also reduces the friction arising during said relative movement between the two components. In addition, because of the low advance force on the front clamping piece 7 and the low necessary braking force on the rear clamping piece 8, the turn-back areas 2d, 2e and the front and rear clamping pieces 7, 8 do not need to be pressed against each other so much in order, for example, to achieve a sealing effect as was previously the case in the prior art, since this sealing effect is already achieved by the cooperation between the bead-shaped turn-back areas 2d, 2e and the endoscope shaft 2. Moreover, the lubricant is forced by the second lubricant delivery device 19 with a predetermined pressure into the cavity between the inner and outer tube section 2a, 2b, 2c, so that by this means the frictional forces are further reduced. In this case, because of the low leakage, an initial lubricating procedure for filling the cavity between the outer and inner roll-back tube section is in some circumstances sufficient, i.e. during at least part of the treatment lubricant does not necessarily have to be forced in.

The cooperation of the friction wheels 14, as a common continuous drive for the roll-back tube 2 and for the endoscope shaft 1, of the front and rear beads as seals together with the endoscope shaft 1, and of the continuous film of lubricant between the inner tube section 2a and the shaft 1, therefore permits an extremely exact and precisely controllable advance of the endoscope shaft 1, which substantially facilitates its handling compared to the prior art.

At this point it should be noted that instead of the rear clamping piece 8, an additional external synchronizing drive mechanism can also be provided, which acts, via a number of friction wheels, on the endoscope shaft 1 at its rear end section and thus ensures the continuous movement of insertion of the endoscope.

Moreover, instead of the friction wheel construction, it is also possible to use, as external synchronizing drive, a spindle drive for controlled continuous advance of the endoscope shaft 1.

The withdrawal of the endoscope takes place essentially in the same way as the insertion procedure, although in this case the front clamping piece 7 takes on the synchronization of the speeds of movement between the endoscope shaft 1 and the roll-back tube 2, while the rear clamping piece 8 is largely free of load.

A second preferred illustrative embodiment of the invention is described hereinafter with reference to FIGS. 2, 2a and 2b, with only those structural details which differ from the first illustrative embodiment being discussed.

Figure 2:
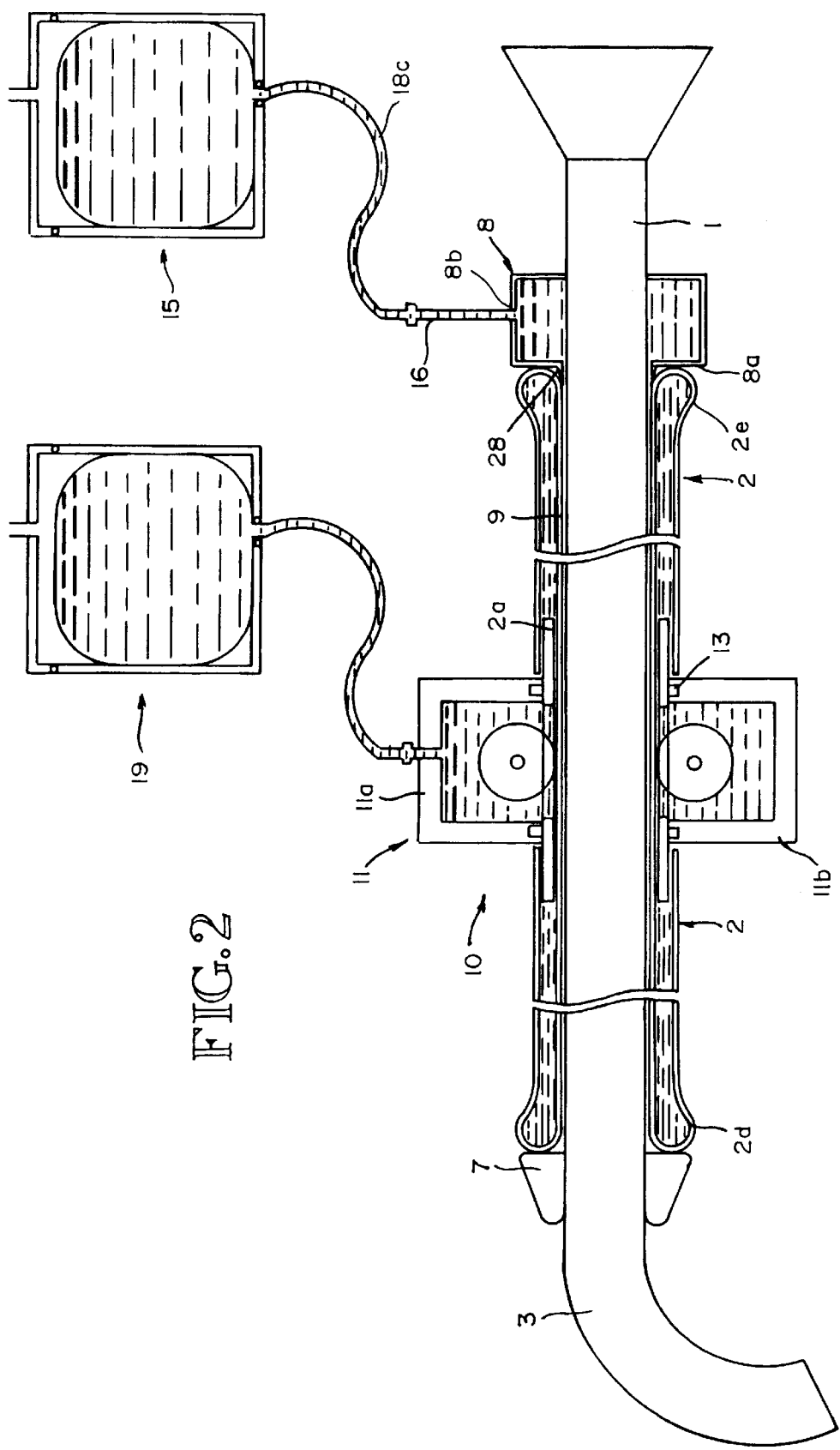
FIG. 2 shows an endoscope with shaft lubrication via a rear clamping piece according to a second illustrative embodiment of the invention, this clamping piece being connected to a lubricant injection shoe.

As is shown in FIG. 2, according to the second illustrative embodiment of the invention the rear clamping piece 8 is designed as a hollow cuff which forms, together with the endoscope shaft 1, an essentially closed cavity. The rear hollow cuff is preferably symmetrically divisible axially into two half shells, so that it can be applied better to the endoscope shaft 1. The side wall or contact wall 8a of the cuff-shaped clamping piece 8, directed toward the roll-back tube 2, has, in the area of the endoscope shaft 1, at least one lubricant injection shoe 28 protruding into the roll-back tube 2. This shoe 28 is shown in particular in FIG. 2b in its cross section. Accordingly, the lubricant injection shoe 28 extends at least over a ⅓ of a circle or over a ½ of a circle about the endoscope shaft 1. Two lubricant injection shoes 28 arranged diametrically in relation to each other are preferably provided, although in FIG. 2b only one shoe is shown. According to FIG. 2a, the above-described cavity can also be replaced, for the sake of simplicity, by a channel for the admission of lubricant. The lubricant injection shoes 28 also lie elastically on the jacket surface of the endoscope shaft 1, at least at their outermost end section, and in each case have at least one lubricant channel, as is shown in FIG. 2a, which, at the rear end (root) of the lubricant injection shoe 28, opens out into the cavity or the admission channel of the cuff, and, at its front free end, opens out into the annular gap 9.

As an alternative to the above-described lubricant injection shoe 28, a number of recesses or notches (not shown in detail) can simply be provided in the side wall 8a of the cuff 8, and these form an outlet gap or column between the endoscope shaft 1 and the contact wall 8a.

In addition, the rear clamping piece 8 is provided with a line attachment 8b which is in fluid communication with the first lubricant delivery device 15 via the admission line 16 and the outlet tube 18c. All other parts of the endoscope according to FIG. 2 correspond to those of the first illustrative embodiment.

During operation of the endoscope according to the second preferred illustrative embodiment of the invention, the first lubricant delivery device 15 delivers the lubricant into the cavity within the rear cuff-shaped clamping piece 8, which fills up accordingly. At a defined pressure within the cavity, the lubricant flows from the lubricant channel inside the lubricant injection shoe 28, or from the gaps in the contact wall 8a, and penetrates into the annular gap 9 between the endoscope shaft 1 and the inner tube section 2a of the roll-back tube 2 for the purpose of lubricating the relative sliding movement of the two components. In order to prevent leakage at the lubricant injection shoe 28 or at the outlet gap of the rear clamping piece 8, the rear turn-back area 2e of the roll-back tube 2 acts as a seal against the shaft 1 and against the contact side 8a of the rear clamping piece 8. The rear roll-back tube area also sealingly encloses off the lubricant injection shoe 28 along its entire length..

By means of this measure it is possible to dispense with the costly installation of channels inside the endoscope shaft 1, as a result of which the handling of the endoscope is further improved.

Finally, as regards the first and second illustrative embodiment of the invention, it should be noted that in particular the driving of the endoscope can be effected by components other than the friction wheels 14. Thus, for example, for the advance mechanism 10 of the roll-back tube 2, toothed wheels could be provided which act on the inner tube section 2a. All these variants have the common feature, however, that the pressing force acting in the radial direction is sufficient to press the inner tube section 2a against the endoscope shaft 1 for its continuous drive despite the presence of lubricant, as a result of which the exact positioning of the distal end at a location which is to be examined is made possible.

Finally, a third preferred illustrative embodiment of the invention is described in detail hereinbelow with reference to FIG. 5, only those components being discussed which are different than the previous illustrative embodiments. All other features correspond to those of the first or second illustrative embodiment.

Figure 5:
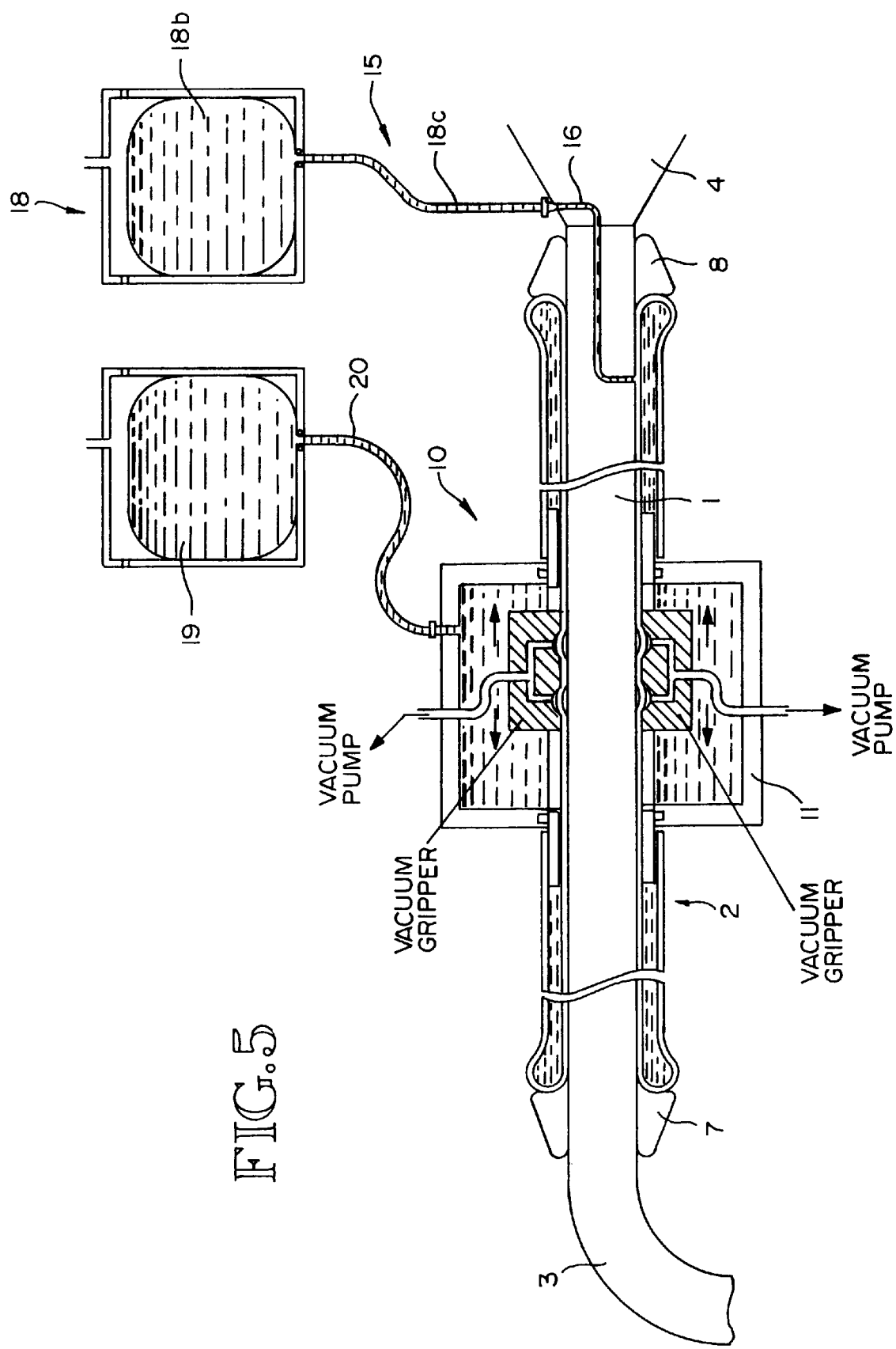
FIGS. 5 and 6 show an endoscope according to a third preferred illustrative embodiment of the invention.

According to FIG. 5, the drive mechanism of the third illustrative embodiment consists of a drive housing 11 which is placed around the tube-guiding sleeve 5, as in the first and second illustrative embodiment, and in which at least two vacuum grippers are arranged so that they can be moved alternately in the axial direction of the endoscope shaft 1. The vacuum grippers consist of small blocks with suction cups which engage through the openings in the drive sleeve 5 and bear tightly on the inner roll-back tube section 2a, which suction cups are formed on that side of the blocks coming into contact with the tube 2a, by means of an underpressure generated by a vacuum pump, suction the tube material in the area of the inner roll-back tube section 2a and thus produce a positive and nonpositive connection with the inner tube section 2a. The vacuum pump (not shown) is for this purpose connected to a vacuum attachment which is formed in the housing 11 of the drive mechanism 10 and is connected to the suction cups via channels inside the blocks. The movement of the blocks, which is effected by a movement mechanism (not shown in detail), and the generation of the underpressure inside the suction cups is controlled in such a way that the blocks are moved to and fro alternately and in the case of more than two blocks continuously at uniform intervals, with corresponding synchronous suctioning and releasing of the inner roll-back tube section 2a, and thus generate a virtually continuous and uniform advance movement of the roll-back tube 2.

As can be seen clearly in FIG. 5, the creation of a vacuum in the suction cups effects a slight lifting of the inner roll-back tube section 2a from the endoscope shaft. The advancing force on the endoscope shaft 1 takes place, in this illustrative embodiment, essentially as in the previous embodiments. The whole arrangement is, as in the first and second illustrative embodiment, filled with a lubricant which assumes the lubrication of the roll-back tube 2.

Figure 6:
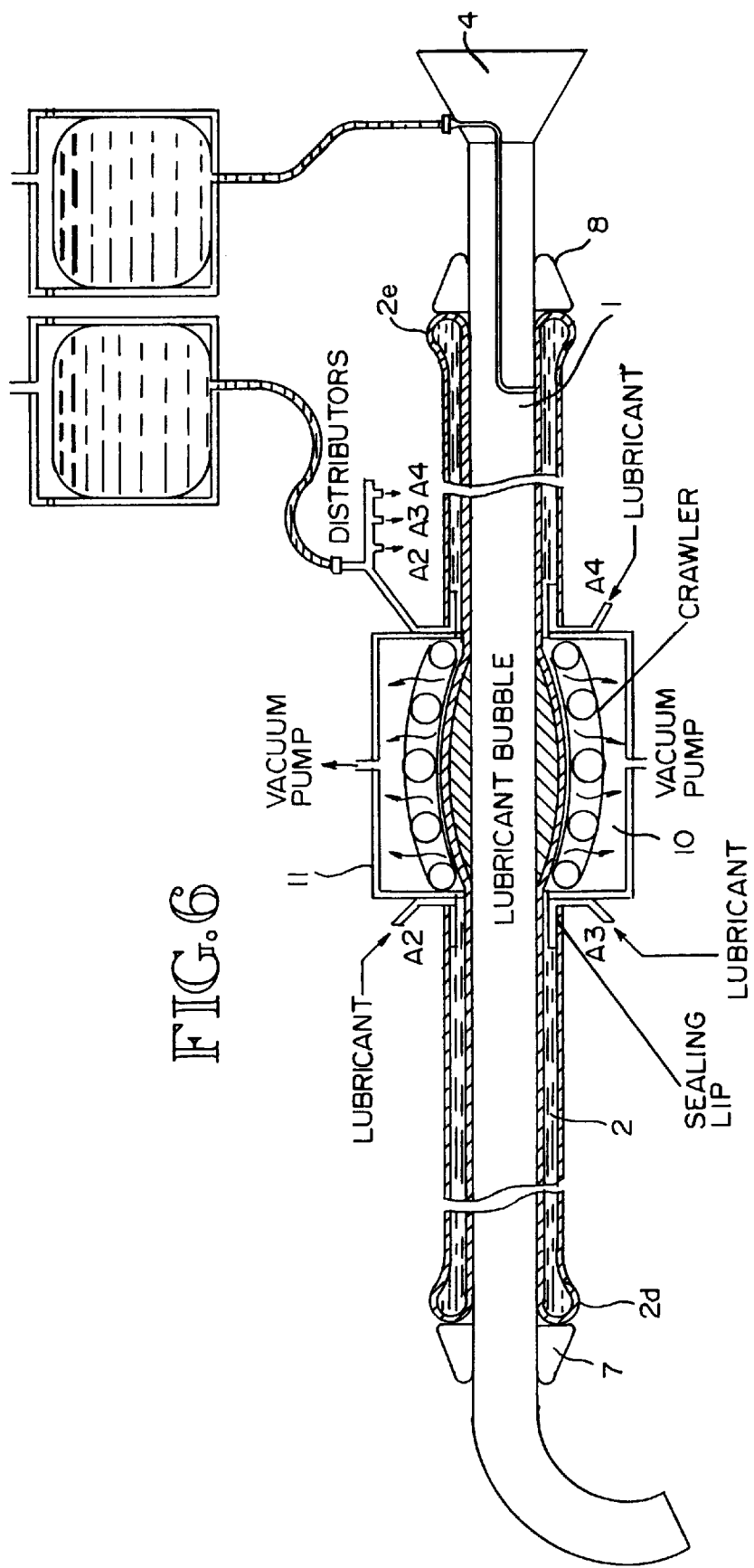

FIG. 6 shows an alternative embodiment to the third illustrative embodiment in which, by generating an underpressure, a driving force can be applied to the roll-back tube.

As can be seen from FIG. 6, the roll-back tube 2 rolled back at both ends forms, together with a housing 11 of the drive mechanism, a one-piece component without the arrangement of a drive sleeve. I.e., in this illustrative embodiment the free ends of the outer front and rear tube sections 2b and 2c are fastened directly and with sealing on the side walls of the drive housing 11.

The drive mechanism of the third illustrative embodiment is formed in this case by a type of crawler drive consisting of at least one elastic continuous belt which is tensioned and driven via at least two wheels spaced apart from each other in the direction of advance. The whole drive mechanism is accommodated in the housing, which is preferably divided in two in the longitudinal direction, can be closed off in an airtight manner and has a suction attachment. The continuous belt has a number of openings or a perforation on its surface. The suction attachment is connected via a tube line to a vacuum pump (not shown).

The housing 11 itself is open on that side directed toward the inner tube section 2a, and the continuous belt is guided in such a way that it closes off the open side of the housing 11 as tightly as possible. Gaps between the side edges of the continuous belt and the housing 11 can be closed off by suitable sealing lips which are fastened on the housing walls and on which the continuous belt slides. In addition, the housing 11 is arranged in such a way, with respect to the roll-back tube 2 fastened thereon, that the outwardly exposed side of the continuous belt orients itself with a small gap or distance above the inner tube section 2a.

When this device is in operation, the interior of the housing 11 is evacuated by the vacuum pump, with air being sucked through the perforation in the continuous belt. At the same time the inner tube section 2a is also sucked and bears sealingly on the outside of the continuous belt. By means of this sealing of the perforation, the underpressure inside the housing increases in such a way that the continuous belt, because of its elasticity, arches inward and in so doing entrains the inner tube section 2a, as is shown clearly in FIG. 6.

By this measure, the inner tube section 2a is held firmly on the continuous belt along the length thereof and is at the same time distanced from the endoscope shaft 1. The advance of the endoscope shaft 1 is thus effected essentially by the contact forces which, during an advance movement of the front outer tube section 2b by the continuous belt, are applied on the front clamping piece 7 at the front turn-back area 2d, in which case the inner tube section 2a remains contactless in particular in the area of the drive unit. Because of the low frictional forces, the necessary advancing force on the front clamping piece 7 is relatively low, so that no creasing (folding) in the front section of the roll-back tube 2 is to be expected. In addition, as in the first and second illustrative embodiment, a lubricant is forced into the annular gap 9, as a result of which the friction is further reduced, in particular in the area of the front and rear sealing beads 2d, 2e.

The third illustrative embodiment, as well as its alternative embodiment variants, accordingly also provides, as in the first and second illustrative embodiment, a continuously or virtually continuously working drive mechanism which acts mechanically on the roll-back tube 2 and ensures an exactly controllable movement of the endoscope.

The invention relates, in summary, to a roll-back tube system, preferably for an endoscope which has an inner shaft which is guided in a roll-back tube of the type rolled back at both ends. The tube is driven via a number of friction wheels, suction cups or crawlers which act on an inner tube section in order to drive the system in a continuous movement. In order to seal the gap between the shaft and the inner tube section, front and rear turn-back areas in each case form a bead which bear sealingly on the shaft. The admission of lubricant into the gap between shaft and inner tube section takes place via an essentially radial shaft bore in the area of the roll-back tube, which is connected either via the shaft cavity or an inner line to an external admission line or via a rear clamping piece by means of a lubricant injection shoe adapted to the shaft surface.

What is claimed is:

1. A roll-back tube system comprising:

an inner shaft having an exterior surface and defining an axis;

a flexible tube formed to slidingly engage a portion of the exterior surface of the inner shaft, the flexible tube having a first end and a second end wherein the first end and the second end are radially convoluted to form a first convolution and a second convolution, respectively, and the first end and the second end are brought towards one another to form first and second outer tube sections and first and second inner tube sections, whereby a first annular void is defined by the first inner tube section and the first outer tube section, and a second annular void is defined by the second inner tube section and the second outer tube section;

a drive housing constructed so as to accept the inner shaft and flexible tube wherein the first end of the flexible tube is linked to a first part of the drive housing and the second end of the flexible tube is linked to a second part of the drive housing; and advancing means disposed in the housing to cause controlled axial movement of the shaft wherein the advancing means is selected from the group consisting of:

at least one driven wheel in compressive contact with the flexible tube so that sufficient friction exists between the at least one driven wheel and the shaft to cause controlled movement of the shaft during operation of the at least one driven wheel;

a first reciprocating suction cup drive movable in the axial direction having at least one orifice formed in a drive member and connectable to a vacuum source wherein the orifice is located proximate to the first or second inner tube section, and a second reciprocating suction cup drive movable in the axial direction located opposite to the first reciprocating suction cup drive; and at least one crawler mechanism comprising at least one driven wheel and a second wheel surrounded by a continuous belt wherein the belt is in frictional contact with a portion of the first or second inner tube section.

2. The system of claim 1 wherein a portion of the first or second inner tube section is in compressive contact with the shaft at a location generally at or proximate to the advancing means.

3. The system of claim 1 wherein the at least one driven wheel is opposed by a second wheel.

4. The system of claim 1 wherein the at least one driven wheel is one of a plurality of wheels spaced about the circumference of the shaft.

5. The system of claim 4 wherein the plurality of wheels are spaced equidistant from one another.

6. The system of claim 1 further comprising a first abutment member frictionally disposed about the shaft and substantially adjacent to the first convolution and a second abutment member frictionally disposed about the shaft and substantially adjacent to the second convolution.

7. The system of claim 1 wherein a second crawler mechanism is located opposite to the at least one crawler mechanism.

8. The system of claim 1 wherein the housing sealing surrounds the inner shaft and flexible tube to create an air tight chamber and forms an orifice, and wherein the continuous belt defines a plurality of perforations, whereby partial evacuation of air in the chamber defined by the housing results in the compression of the first or second inner surface against the belt of the crawler mechanism.

9. The system of claim 8 further comprising a first abutment member frictionally disposed about the shaft and substantially adjacent to the first convolution and a second abutment member frictionally disposed about the shaft and substantially adjacent to the second convolution.

10. The system of claim 1 further comprising a member for synchronizing the movement of the inner shaft with the movement of the flexible tube.

11. The system of claim 10 wherein the synchronizing member is selected from the group consisting of a roller drive acting on the inner shaft and cooperatively linked to the advancing means, and at least one abutment member frictionally disposed about the shaft and substantially adjacent to a flexible tube convolution.

12. The system of claim 1 further comprising a drive sleeve having an exterior surface, an interior surface, a first end, and a second end, and linking the first and second ends of the flexible tube to the housing, wherein the drive sleeve is coaxially intermediate the housing and at least the first and second inner tube sections.

13. The system of claim 12 wherein the housing coaxially surrounds the drive sleeve and is sealingly mated thereto.

14. The system of claim 12 wherein the drive sleeve defines at least one slot to expose a portion of the inner tube section to the advancing means.

15. The system of claim 12 wherein the drive sleeve defines a plurality of slots, the number and location of which correspond to the number and location of wheels.

16. The system of claim 15 wherein the first end of the flexible tube is affixed to the exterior surface of the first end of the drive sleeve, and the second end of the flexible tube is affixed to the exterior surface of the second end of the drive sleeve.

17. The system of claim 12 wherein the drive sleeve interior surface defines at least one groove extending substantially from the first end to the second end.

18. The system of claim 12 wherein the drive sleeve interior surface defines a plurality of grooves extending substantially from the first end to the second end.

19. The system of claim 12 wherein the first end of the flexible tube is affixed to the exterior surface of the first end of the drive sleeve, and the second end of the flexible tube is affixed to the exterior surface of the second end of the drive sleeve.

20. An endoscope with a roll-back tube system comprising:
   an articulable shaft having an exterior surface and defining an axis;
   a flexible tube formed to slidingly engage a portion of the exterior surface of the shaft, the flexible tube having a first end and a second end wherein the first end and the second end are radially outwardly convoluted to form a first convolution and a second convolution, respectively, and the first end and the second end are brought towards one another to form first and second outer tube sections and first and second inner tube sections, whereby a first annular void is defined by the first inner tube section and the first outer tube section, and a second annular void is defined by the second inner tube section and the second outer tube section;
   a drive sleeve having an exterior surface, an interior surface, a first end, and a second end, wherein the first end of the flexible tube is attached to the first end exterior surface of the drive sleeve and the second end of the flexible tube is attached to the second end exterior surface of the drive sleeve, and wherein the first or second inner tube sections pass proximate to the interior surface of the sleeve during axial movement of the sleeve;
   a drive housing surrounding the shaft and drive sleeve; and
   advancing means disposed in the housing to cause controlled axial movement of the shaft wherein the advancing means frictionally engages the flexible tube.

21. The endoscope of claim 20 wherein the drive sleeve defines at least two slots to expose the flexible tube to the advancing means, and wherein the advancing means comprises at least two wheels extending into the corresponding slots and in compressive contact with the flexible tube, at least one wheel being driven by a source of motive power to impart axial motion thereof and of the shaft.

22. The endoscope of claim 20 wherein the drive housing defines a chamber and sealingly surrounds the drive sleeve.

23. The endoscope of claim 22 wherein the interior surface of the drive sleeve defines at least one groove extending substantially from the first end of the sleeve to the second end of the sleeve, thereby permitting fluid communication between the drive housing chamber and the first annular void and the second annular void.

24. The endoscope of claim 20 further comprising a fluid reservoir fluidly coupled to the annular space defined by the exterior surface of the shaft and the first and the second inner tube sections.

25. The endoscope of claim 20 further comprising a first abutment member frictionally disposed about the shaft and substantially adjacent to the first convolution and a second abutment member frictionally disposed about the shaft and substantially adjacent to the second convolution.

26. The endoscope of claim 25 wherein the drive sleeve defines at least two slots to expose the flexible tube to the advancing means, wherein the advancing means comprises at least two wheels extending into the corresponding slots and in compressive contact with the flexible tube, at least one wheel being driven by a source of motive power to impart axial motion thereof and of the shaft, wherein the drive housing defines a chamber and sealingly surrounds the drive, and wherein the interior surface of the drive sleeve defines at least one groove extending substantially from the first end of the sleeve to the second end of the sleeve, thereby permitting fluid communication between the drive housing chamber and the first annular void and the second annular void.

27. The endoscope of claim 26 further comprising a first fluid reservoir fluidly coupled to the annular space defined by the exterior surface of the shaft and the first and the second inner tube sections and a second fluid reservoir fluidly coupled to the chamber defined by the drive housing.

* * * * *